(12) United States Patent
Corria Osorio et al.

(10) Patent No.: US 9,701,730 B2
(45) Date of Patent: Jul. 11, 2017

(54) TGFβ-DERIVED POLYPEPTIDES AND USES THEREOF

(71) Applicant: CENTRO DE INMUNOLOGIA MOLECULAR, Havana (CU)

(72) Inventors: Ángel de Jesús Corria Osorio, Granma (CU); Kalet León Monzón, Havana (CU); Tania Carmenate Portilla, Havana (CU); Amaury Pupo Meriño, Havana (CU); Saumel Pérez Rodríguez, Artemisa (CU)

(73) Assignee: Centro De Inmunologia Molecular, Habana, Havana (CU)

( * ) Notice: Subject to any disclaimer, the term of this patent is extended or adjusted under 35 U.S.C. 154(b) by 0 days.

(21) Appl. No.: 14/440,627

(22) PCT Filed: Oct. 30, 2013

(86) PCT No.: PCT/CU2013/000007
§ 371 (c)(1),
(2) Date: May 5, 2015

(87) PCT Pub. No.: WO2014/071894
PCT Pub. Date: May 15, 2014

(65) Prior Publication Data
US 2015/0284441 A1    Oct. 8, 2015

(30) Foreign Application Priority Data

Nov. 9, 2012  (CU) .......................... CU/P/2012/0158

(51) Int. Cl.
*C07K 14/495* (2006.01)
*A61K 39/39* (2006.01)
*A61K 47/48* (2006.01)
*A61K 38/18* (2006.01)

(52) U.S. Cl.
CPC ........ *C07K 14/495* (2013.01); *A61K 38/1841* (2013.01); *A61K 39/39* (2013.01); *A61K 47/48215* (2013.01); *A61K 47/48415* (2013.01)

(58) Field of Classification Search
None
See application file for complete search history.

(56) References Cited

U.S. PATENT DOCUMENTS

2002/0169292 A1*  11/2002  Weintraub ............. C07K 14/47
530/397

OTHER PUBLICATIONS

Radaev et al. Ternary complex of transforming growth factor-beta1 reveals isoform-specific ligand recognition and receptor recruitment in the superfamily. J Biol Chem. May 7, 2010;285(19):14806-14. Epub Mar. 5, 2010.*
Flower DR. Receptor-binding sites: bioinformatic approaches. Methods Mol Biol. 2006;316:291-358.*

* cited by examiner

*Primary Examiner* — David Romeo
(74) *Attorney, Agent, or Firm* — Rothwell, Figg, Ernst & Manbeck, P.C.

(57) ABSTRACT

The present invention relates to the field of Biotechnology and more particularly to the mutated polypeptides of TGFβ molecule whose primary sequence has a high homology with the sequence of human TGFβ. These muteins lose their ability to interact with ALK5 but maintain their ability to interact with other receptors that are part of the receptor complex (TβRII and TβRIII). They have the property of antagonizing the signaling of all natural variants of TGFβ ligands, dependent of ALK5 recruitment in the receptor complex, and have significant immunomodulatory effects. The present invention relates to pharmaceutical compositions comprising as active principle the polypeptides or fusion proteins disclosed and their use thereof given their modulating effect on the immune system in diseases such as cancer, diseases accompanied by fibrosis and chronic infectious diseases.

14 Claims, 6 Drawing Sheets

Neutralization of the Inhibition of CTLL2 proliferation induced by rTGFβ1

Figura 6
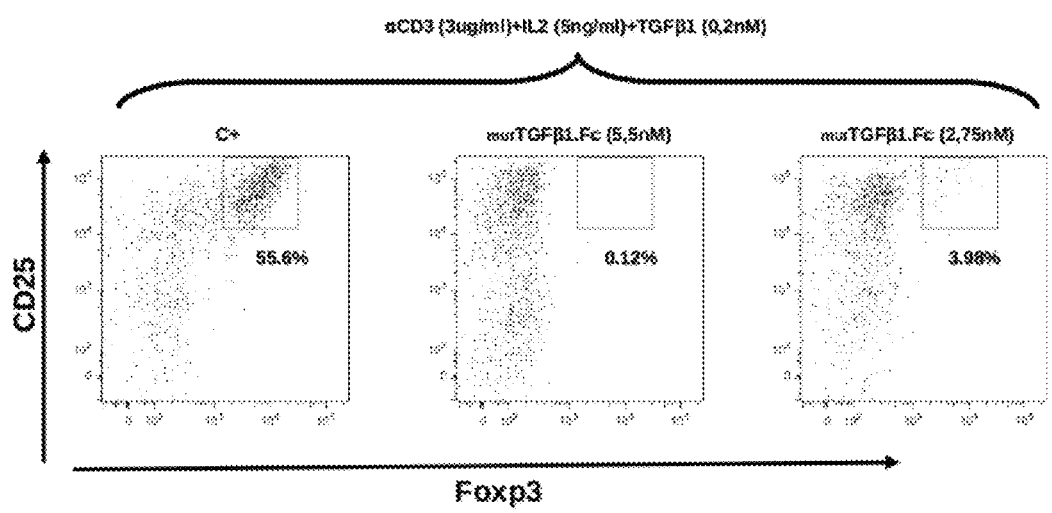

TGFβ-DERIVED POLYPEPTIDES AND USES THEREOF

CROSS REFERENCE TO RELATED APPLICATION

This application is a 35 U.S.C. 371 National Phase Entry Application from PCT/CU2013/000007, filed Oct. 30, 2013, which claims the benefit of Cuban Patent Application No. CU-2012-0158 filed on Nov. 9, 2012, the disclosure of which is incorporated herein in its entirety by reference.

SCOPE OF THE TECHNIQUE

The present invention relates to the fields of Biotechnology and Medicine. Particularly to the use of mutated variants of TGFβ molecule, which are antagonists of the signaling of their natural counterparts, and to the therapeutic application of these variants.

BACKGROUND

TGFβ cytokines were discovered by their capacity to stimulate cell colony formation (Roberts A B, et al, Proc Natl Acad Sci USA 78: 5339-43, 1981); because this process is a classic marker of cellular transformation, this molecule was called Transforming Growth Factor beta. Nowadays TGFβ ligands (TGFβ1, TGFβ2, TGFβ3) are recognized as the prototype of multifunctional growth factors. Almost any type of cell in the body produces them and expresses its receptor complex. These molecules are potent inhibitors of the proliferation of epithelial, endothelial and hematopoietic cells (Ravitz, M J et al, Adv Cancer Res 71: 165-207, 1997) and they are one of the most potent regulators of extracellular matrix production and deposition (Massague, J. The Annu Rev Cell Biol 6: 597-641, 1990) and of tissue repair cascade (Roberts A B., and others, 275-308 Plenum, 1996). They also regulate various mechanisms during embryonic development such as cell differentiation, migration and angiogenesis. (Taya, Y. at al, Development 126: 3869-79, 1999; Lidral, A. et al Am J Hum Genet 63: 557-68, 1998)

In the immune system the TGFβ signaling is a very important regulation node. One of its most important functions is maintaining lymphocyte homeostasis and immune tolerance, through inhibition of the proliferation of naïve T cells induced by self-antigens in lymphopenic environments. (Bevan, M. et al, Nat Immunol. 27, 13 (7): 667-73, 2012). This molecule also suppresses or alters the activation, maturation and differentiation of natural killer cells (Laouar, Y. et al Nature Immunol 6: 600-607, 2005), dendritic cells (Luo, X. et al, Proc. Natl Acad. Sci USA 104: 2821-2826, 2007; Bekeredjian Ding, I. et al, Immunology 128: 439-450, 2009), macrophages (Sica, A. et al, Semin. Cancer Biol 18, 349-355, 2008, Torroella. M et al, Cancer Res 69: 4800-09, 2009), neutrophils (Fridlender, Z G et al, Cancer cell 16: 183-194, 2009) and effector and memory T cells (Gorelik, L. & Flavell, R A Nature Med, 7: 1118-1122, 2001; Flavell, R A Immunity 31:131-44, 2009). The TGFβ plays an essential role in the induction, differentiation and maintenance of natural and induced regulatory T cells (CD4+Foxp3+) and TCD4+IL17+(TH17) effector T cells (Kryczek, I. et al, J. Immunol. 178 : 6730-33, 2007; Moo-Young, T A et al. J. Immunother 32: 12-21, 2009; Fantini, M C et al J. Immunol. 172: 5149-53, 2004; Flavell, R. A. Cell 134: 392-404, 2008).

Mature TGFβ ligands are homodimers of 112 amino acid residues. They are derived from a precursor molecule formed by the latency associated pro-peptide (LAP) located at N-terminal and the active domain towards the C-terminus extreme. Both domains are intracellularly separated by proteolysis and the ligands are secreted as inactive precursors, formed by the prodomain reversibly bound to the active domain, thus regulating access to cellular receptors (Geoffrey D. Young and Joanne E. Murphy-Ullrich. JBC Vol 279, No. 36: 38032-39, 2004). It has been postulated that the pro-peptide associated to latency is also important for secretion of the mature domain (Gray A. and A Mason Science 247:1328-30, 1990).

All three isoforms (TGFβ1, TGFβ2, TGFβ3) interact in the plasma membrane with receptors TβRI, TβRII and TβRIII. The latter, also known as Betaglycan, is not expressed in all cell types, and although it is dispensable for the signaling mediated by TGFβ1 and TGFβ3 ligands, constitutes a reservoir of these ligands when TβRII is saturated. (Wang X F et al, Cell 67: 797-805, 1991; Lebrin F. et al Cardiovasc. Res 65: 599-608, 2005). TβRIII forms complexes with TβRI and TβRII receptors presenting the ligand to them. These receptors bind primarily to TβRII and the TβRII/TGFβ complex recruits and activates cooperatively and with high affinity TβRI receptor, resulting in the formation of a signaling hetero-trimeric complex. TGFβ1 and TGFβ3 can bind to TβRII with high affinity (5-30 pm), while TGF-β2 can only do it in the same way in the presence of TβRIII (De Crescenzo et al, J Biol Chem 279: 26013-18, 2004; De Crescenzo et al, J. Mol. Biol 328: 1173-1183, 2003; Groppe et al, Molecular Cell 29, 157-168, 2008).

So far it has not been reported that ligands of TGFβ1, TGFβ2 and TGFβ3 families have the capacity to bind to other type II receptors, which are part of the same protein family TβRII belongs to (Huang F and Y G Chen Cell Biosc Mar. 15, 2:9, 2012). However they can bind with several type I receptors. ALK5 is described as the reference TβRI receptor of its ligand subfamily. After its recruitment into the TβRII/TGFβ complex the phosphorylation of SMAD2/3 proteins is induced (Huang F and Y G Chen Cell Biosc; Mar. 15, 2:9, 2012). ALK1 is activated in response to the formation of the TGF/TβRII complex in endothelial cells and signals by SMAD1 and SMAD5 (Goumans M J et al, Mol Cell 12 (4): 817-28, 2003). In some epithelial cells the SMAD1/5 signaling is induced by receptor ALK2, ALK3 and ALK6 (Daly A C et al, Mol Cell Biol, 28: 6889-6902, 2008). ALK2 is also associated with processes related to in vivo cardiovascular development (Olivey H E et al, Dev Dyn 235 (1): 50-9, 2006). We should highlight that both TβRII and ALK5 are unique to TGFβ1, TGFβ2 and TGF β3 family of ligands while ALK1/2/6/3 are more promiscuous and also shared by Activins and Bone Morphogenetic Proteins (Sebald W. et al, Biol Chem, 385 (8): 697-710, 2004).

ALK5 mediated signaling is associated with various pathogenic mechanisms in certain diseases. In cancer, for example, its role is complex and is associated with the suppression of immune response and promotion of tumor progression. The suppression of immune response occurs mainly during early stages of tumorigenesis. While its role as tumor progressor occurs in advanced stages of the carcinogenesis, through the induction of metastatic invasive phenotypes and the suppression of anti-tumor immune response (Miyazono K. Nat Rev. Cancer 10: 415-24, 2010; Miyazono K. Cancer Sci 101 (2): 306-12, 2010; Hawinkels L J. et al, Growth Factors 29(4):140-52, 2011). Another illness in which of TGFβ's activity is also deleterious are chronic infections caused by pathogens such as HIV, HBV, HCV, CMV, mycobacteria and *Trypanosoma cruzi* parasite. The TGFβ exerts a negative influence on the protective immune response, allowing growth and survival of these intracellular pathogens (Reed G S. Microbes and Infection 1: 1313-1325, 1999). In many diseases overproduction of TGFβ contributes to pathological excess of fibrotic tissue, which compromises the normal function of the damaged organ. Some examples of pathological excess of fibrotic tissues are pulmonary fibrosis, sarcoidosis, cardiac fibrosis, cardiomyopathy, liver cirrhosis, systemic sclerosis, glomerular sclerosis and primary biliary cirrhosis, among others (Kopp J B et al, Microbes and Infection, 1: 1349-1365, 1999).

Multiple strategies have been designed to inhibit TGFβ signaling. Most inhibitors have been evaluated in preclinical models, although some of them have begun to be tested in various types of cancer and fibrosis in clinical trials (Flavell R A. Nat Rev Immunol. 10(8): 554-67, 2010; Connolly E C et al, Int J Biol Sci 8(7): 964-78, 2012; Hawinkels L J. et al, Growth Factors 29 (4): 140-52, 2011). In the state of the art you may find the following inhibition strategies:

1—Neutralization of the ligands using soluble forms of the extracellular domains of its receptors (US 2002/0004037 and US 2007/0244042), anti-TGFβ antibodies (US 2002/076858, US 2005/0276802) or oligonucleotides that block transduction of cytokine genes (US 2004/0006036 US2007/0155685).
2—Blockade of signaling using small molecules that bind to the kinase domain of TβRI/ALK5 (US 2006/0057145, US 2005/0136043, US 2006/0234911)
3—Receptor II blockade with antibodies that recognize its extracellular domain (US 2010/0119516, US 2009/7579186).

So far an inhibition strategy using muteins of ligands TGFβ as signaling antagonists has not been reported.

BRIEF DESCRIPTION OF THE INVENTION

The present invention is related to the scientific finding that mutated variants of the TGFβ family (TGFβ1, TGFβ2 and TGFβ3) may inhibit the function of their natural counterparts. The inventors found for the first time in in vitro experiments that the mutated variants of TGFβ can substantially inhibit the signaling induced by native variants and thus neutralize its biological effects. This finding provides the basis of a new strategy for modulating TGFβ signaling in diseases such as cancer, fibrosis or chronic infection in which these ligands have deleterious activity.

The present invention is about polypeptides with high homology at the level of primary sequence with the human TGFβ, except in some positions where the native amino acid have been mutated to eliminate or to decrease substantially their ability to signal through the ALK5 type 1 receptor. These mutated variants of TGFβ maintain its capacity to bind with high affinity to TβRII and TβRIII receptors, but are unable to signal because they do not interact with the ALK5 type I receptor, negatively modulating natural variants signaling by competing with them for binding to high affinity TβRII and TβRIII receptors. The invention also includes the therapeutic applications of these mutated variants, alone or in combination with vaccines or other therapeutic modalities for the treatment of diseases such as cancer, fibrosis or chronic infections in which the action of TGFβ influences the course of the disease.

The novelty of the present invention is that it provides a novel therapeutic approach to modulate TGFβ signaling and thus modulate the invasive and metastatic capacity of various tumor and the activity of various immune system and connective tissue cells, in diseases where the function of TGFβ reduce the protective immune response either natural or induced by vaccination or inducing an excessive tissue repair and fibrosis. None of the inhibition strategies mentioned above uses muteins of TGFβ ligands as signaling antagonists. TGFβ mutants of the present invention are virtually self-proteins and therefore have low immunogenicity, which minimizes the risk of antibody responses against them. Their high specificity for the TGFβ receptor system reduces unexpected toxicities (common in strategies based in small size inhibitors). These mutated variants of TGFβ maintain binding affinities to TβRII receptor at least as native TGFβ1 and TGFβ3 (6-10 pM). This affinity is hard to achieve with other receptor or ligand inhibition strategies, with monoclonal antibodies or other drugs. Surprisingly the authors of the present invention found that these TGFβ mutated variants maintain their ability to interact with TβRII and TβRIII receptor, which constitutes an advantage over TβRII anti-receptor antibodies, since muteins block all possible binding sites of natural ligands to cell surface.

DETAILED DESCRIPTION OF THE INVENTION

The present invention relates to polypeptides that antagonize the activity mediated by the ALK5 receptor of TGFβ natural ligands. These polypeptides possess homology greater than 90% with respect to the amino acid sequence of TGFβ natural ligands. The polypeptides of the present invention have at least one mutation in their primary amino acid sequence, in one of the residues selected from the group consisting of Y6, W30, W32, I51, L51, Q67 and L101.

In a particular embodiment of the invention the original amino acid residue is mutated by one of amino acid residues selected from the group comprising;

for position 6: A
for position 30: N, R, K, D, Q, L, S, P, V, I, G, C, T, A, E;
for position 32: A;
for position 51: Q, W, Y, A;
for position 67: H, F, Y, W and
for position 101: A, E;

It is another object of the present invention polypeptides in which mutations were added in the interaction interface with receptors TGFβRII and/or TGFβRIII increasing its affinity to them.

Furthermore, the present invention relates to pharmaceutical compositions used for the treatment of cancer, diseases accompanied by fibrosis and chronic infectious diseases that contain one or a mixture of the polypeptides described in the present invention and a pharmaceutically suitable vehicle for their administration. Such polypeptides may be covalently linked to a carrier protein, which may be Albumin or the Fc region of human immunoglobulins. In another embodiment of the present invention the polypeptides may be pegylated.

Finally the present invention relates to the use of the polypeptides described to manufacture a pharmaceutical composition, useful in the treatment of cancer, diseases accompanied by fibrosis and chronic infectious diseases, as well as to enhance the cellular and/or humoral response to vaccines in replacement of native TGFβ especially when the vaccine to potentiate is a therapeutic vaccine for cancer treatment.

Obtaining TGFβ Mutant Polypeptides

The present invention relates to polypeptides having 112 amino acids in length. These polypeptides maintain a high sequence identity with the different native TGFβ molecules, more than 90% identity. In a zone of their sequence, the polypeptides include 1-6 mutations as compared to native TGFβ. The residues that replace the original residues are selected to have very different physicochemical properties with respect to the original amino acid, a change in the residue from nonpolar to polar, from charged to uncharged, from large to small and from acid to basic.

These polypeptides, which may also be called TGFβ muteins, were designed based on the three dimensional structure of native TGFβ1, TGFβ2 and TGFβ3 in complex with their receptors TβRII and ALK5 (and entered in the PDB database). Mutations were introduced only at TGFβ positions corresponding to amino acids significantly exposed to the solvent that form part of the ALK5 receptor binding region but not that of TβRII receptor. These residues were predicted to be important in the interaction with ALK5 using bioinformatic programs of public domain. The following table shows residues from the binding interface to ALK5 that are predicted to be important in the interaction and the possible mutations that affect the binding. With these results a database of all possible theoretical muteins was made and the muteins with the highest antagonist potency in vitro were selected

TABLE 1

Amino acids in TGFβ sequence important for TβRI/ALK5 interaction and mutations that according to the theoretical prediction will destabilize the binding.

| TGFβ residue | Evolutionary Conservation | Mutations |
|---|---|---|
| W30 | Identical conserved | N, R, K, D, Q, L, S, P, V, I, G, C, T, A, E |
| W32 | Identical conserved | A |
| L101 | Identical conserved | A, E |
| I51 | Identical conserved | Q, W, Y, A |
| Q67 | Non-conserved | H, F, Y, W |
| Y6 | Non-conserved | A |

The polypeptides of this invention can be obtained by various procedures including chemical synthesis of proteins. They may also be obtained by genetic engineering techniques, such as expressing them as inclusion bodies in bacteria such as *E. coli* or in mammalian cells such as CHO and HEK293 using any transfection protocol reflected in the art of the technique. Mutations at specific positions may also be obtained by directed mutagenesis techniques directed by means of reaction of the polymerase chain.

Selection of TGFβ Mutant Polypeptides According to their Biological Activity;

The polypeptides of the present invention are selected from the in vitro and in vivo experiments to simultaneously possess the following properties:

- These mutated variants of TGFβ also referred to as muteins in the present invention, maintain their ability to bind to TβRII receptor. This binding ability may be evaluated directly by means of an ELISA assay, which is commercially available, to detect TβRII receptor chain or indirectly on receptor-positive cell populations. The levels of TβRII receptor recognition should be comparable to those of the native TGFβ.
- These muteins block the binding of TGFβ ligands (TGFβ1, TGFβ2, TGFβ3) to TβRII receptor. This can be measured directly by a competitive ELISA covering the plates with each of the TGFβ ligands (commercially available) and assessing the ability of the mutein to inhibit TβRII binding to the ligands.
- These mutated variants of TGFβ loose or substantially reduce their ability to signal through the TβRI receptor. This property can be evaluated directly by Western immunoblotting assays quantifying the levels of phosphorylated Smad2 and Smad3 in tumor cell lysates of 4T1 murine line and MDA-MB231 human line treated with the muteins or with native TGFβ. These muteins should induce the phosphorylation of Smad2 and Smad3 at least 100 times less than the native TGFβ. The property of inducing fosforilation can also be evaluated in vitro in inhibition assays of the proliferation induced by IL-2 on CTLL-2 cell line. These mutants should have an inhibitory activity at least 100 times lower than that of the native TGFβ.
- These mutated variants of TGFβ are capable of inhibiting signaling induced by each TGFβ ligand (TGFβ1, TGFβ2, TGFβ3). This property can be evaluated directly by Western immunoblotting assays quantifying the levels of phosphorylated Smad2 and Smad3 in tumor cell lysates of 4T1 murine line and MDA-MB231 human line treated with the muteins or with native TGFβ. In a concentration range of 50 ng/mL-10 μg/mL the muteins should exhibit an ability to inhibit at least 100 times the signaling induced by the commercial ligands.
- These TGFβ mutated variants have an in vitro antitumor effect. They can inhibit the migration of several tumor cell lines treated or not with the native ligand. Examples of these lines are 4T1 murine line and MDA-MB231 human line. In cell migration assays, these muteins should be able to inhibit significantly from a statistical point of view the migration of tumor cells.
- These mutated variants of TGFβ loose or substantially reduce their ability to induce the differentiation of naive T CD4+ cells to Treg foxp3+ or TH17 phenotypes in the presence of IL-2 or IL-6 and IL-23 respectively. This property can be evaluated directly in in vitro Treg and Th17 cells induction assays. These mutants should have an inducing capacity at least 100 times lower than that if native TGFβ.

These TGFβ mutated variants have the ability to inhibit the differentiation of naive T CD4+ cells to Treg foxp3+ or TH17 phenotypes induced by their natural analogs. This property can be evaluated directly in in vitro Treg and Th17 cells induction assays. In a concentration range of 50 ng/mL-10 μg/mL these muteins should exhibit the ability to inhibit at least 100 times the signaling induced by commercial ligands.

- These mutated variants of TGFβ have an in vivo antitumor effect. They can inhibit in vivo tumor growth and the metastatic ability of several tumor lines in a transplantable tumor model. This property can be evaluated using a primary orthotopic tumor model of 4T1 breast line in BALB/c mice and in MDA-MB231 human tumor cell line in nude mice. These muteins should cause a statistically significant reduction of tumor size and number of lung metastases as compared to the control group treated with PBS.
- These mutated TGFβ variants have the ability to increase in vivo natural or induced by vaccination antitumor immune response in a transplantable tumor model.
  This property can be evaluated using an orthotopic primary tumor model of 4T1 breast line and subcutaneous CT26 colon tumor line, in BALB/c mice. These muteins should increase the cytolytic activity and cytokine secretion of natural killer cells and T CD8+ lymphocytes. They should also increase the activity of dendritic cells and TH1 pattern T CD4+ cells and significantly reduce the number of regulatory T cells and myeloid suppressor cells and their protumoral activity.

The present invention encompasses additional modifications of the TGFβ muteins from which the mature domain lacking LAP could be produced, without affecting the secretion thereof. This entails that the muteins can be obtained in their active form so that they interact with TβRII, which results in the simplification of the production process.

In another embodiment the present invention relates to additional modifications of TGFβ muteins that increase their half-life. These modifications include pegylation, the fusion of any of the above-described immunomodulatory polypeptides to a carrier protein, which can be Albumin or the Fc region of human immunoglobulins, among others.

In a more particular embodiment the present invention relates to mutated variants of TGFβ (specific mutations are referred to in Table 2) fused to an Fc fragment of a human IgG1 which results in a mutein that has been selected to display the properties referred to above. The Fc region selected for the coupling has a set of mutations (ala234, ala235) on the Cγ2 domain that prevent it from interacting with Fc gamma receptors, except with the neonatal Fc receptor, thus silencing its ability to induce immune effector mechanisms (Labrijn A F et al, Curr Opin Immunol. Aug. 20 (4):479-85, 2008. Epub 2008 Jul. 9).

These muteins have multiple amino acid substitutions that significantly reduce their ability to signal through ALK5. However, they maintain its ability to bind to TβRII and TβRIII, and inhibit the activity of native TGFβ.

TABLE 2

Mutant constructed, referring the mutation according to human TGFβ numbering.

| Mutations | Reference Name |
|---|---|
| W30E, L101E, I51Q | G_M1 |
| W30E, L101A, L51Q | G_M2 |
| W30E, L101E, I51Q, Q67H | G_M3 |
| W30E, L101A, K97D, E12H, I51Q, Q67H | G_M4 |

In another embodiment the present invention also encompasses additional modifications of TGFβ muteins, made in order to either increase their affinity to TβRII and TβRIII, but without affecting or even improving their inhibitor character, or to improve their in vivo pharmacodynamic with the increase of half-life. Such additional mutations may be obtained by rational design with bioinformatics tools or using combinatorial molecular libraries of different nature (phage display libraries, libraries of gene expression in yeast or bacteria).

Therapeutic Application of the TGFβ Mutant Polypeptides

This invention also includes the pharmaceutical compositions comprising as active principle TGFβ muteins and their analogs or the fusion proteins disclosed by the present invention as well as their possible therapeutic applications for the modulation of the invasive and metastatic capacity of various tumors and the activity of various immune system and connective tissue cells in diseases in which the functions of TGFβ reduce the protective immune response, either natural or induced by vaccination, or induce an excessive tissue repair and fibrosis.

For their therapeutic use, the polypeptides of the present invention can be administered to a subject carrying a disease independently or combined with other polypeptides or other substances that facilitate or enhance its therapeutic action. The administration route may be any of administration routes described in the art of the technique for parenteral administration of drugs.

The polypeptides may be preferably administered intravenously, intramuscularly, subcutaneously or intratumorally.

The polypeptides or fusion proteins described in the present invention can also be administered as part of a pharmaceutical composition useful in the therapy of cancer, diseases accompanied by fibrosis and chronic infectious diseases. Preferably, the present invention encompasses compositions, including pharmaceutical compositions, comprising a pharmaceutically acceptable vehicle.

The composition includes pharmaceutically acceptable carriers. The pharmaceutically acceptable carriers include, but are not limited to: saline, sterile water, phosphate buffered saline, and similars. Other buffering agents, dispersed agents and inert non-toxic substances suitable for administration to a patient may be included in the compositions of the present invention. The compositions may be appropriate solutions for the administration and are sterile and free of unwanted particles.

In another embodiment the present invention also relates to methods of treatment comprising the administration of a therapeutically effective amount of polypeptides, fusion proteins or compositions described in this invention to subjects with cancer, diseases accompanied by fibrosis or chronic infectious diseases. In a particular embodiment the subject is a human being.

The polypeptides or fusion proteins described by the present invention may also be administered in combination with traditional oncological therapies (chemotherapy and radiation) as an enhancer of the effect of these.

To obtain the desired therapeutic effect, the polypeptides of the present invention should be administered at doses high enough to guarantee that their concentration in the lymph node or peripheral site is appropriate for the disease of interest, that is, in the concentration range in which mutein shows an inhibitory effect of native TGFβ. The dose must therefore be adjusted to the type of disease and route of administration being studied. For example, in the case of tumor therapy, the dose should be adjusted to achieve mutant concentrations inside the tumor and/or loco-regional lymph node high enough to exhibit an inhibitory effect. Dose ranges to be explored may vary between 1.25-20 mg/kg/dose weekly or biweekly.

The number of administrations should also be adjusted to the biodistribution of the mutein in question. In general the aforementioned effective concentrations should be sustained for a time period ranging from 2 to 30 consecutive days. If the mutein is coupled to a carrier protein, the frequency of administration should be adjusted accordingly.

When a compound or a composition of the invention is used in combination with another anticancer agent, the present invention provides, for example, concurrent, staggered or alternated treatment options. Thus, the compound/s of the invention may be administered simultaneously in separate pharmaceutical compositions, that is, a compound of the invention may be administered before or after the other anticancer agent, for example, with a difference of seconds, minutes, hours, days or weeks.

Therapeutic action is defined as full or partial remission of the symptoms of a disease. In cancer, therapeutic action is defined as a decrease in tumor volume or increase in relapse time, amongst others.

This novel therapeutic strategy has many advantages of over other proposals for modulating TGFβ signaling. For example:

- TGFβ mutants are virtually self-proteins (except for a few mutations) and therefore have low immunogenicity. This fact minimizes the risk of antibody responses against them.
- Their high specificity by the TGFβ receptor system reduces unexpected toxicities, which are common in strategies based on small size inhibitors.
- These mutated variants of TGFβ maintain binding affinities to TβRII receptor at least as native TGFβ1 and TGFβ3 (6-10 pM). This affinity is hard to beat with receptor or ligand inhibition strategies, with monoclonal antibodies or other drugs.
- These mutated variants of TGFβ have a smaller size than monoclonal antibodies and receptors coupled to Fc. This feature ensures a better penetration to the tumor than the others drugs that inhibit the TGFβ signaling and described above.
- These mutated variants of TGFβ inhibit signaling of any ligand through TβRII/TβRI (ALK5) receptor system, which is a theoretical advantage over pan-ligand antibodies, because these are directed only to known TGFβ isoforms, if other isoforms exist these antibodies may not inhibit them.
- TGFβ mutated variants maintain the ability to interact with TβRIII receptor. This constitutes an advantage over TβRII anti-receptor antibodies, because these muteins block all possible binding sites of natural TGFβ ligands to the cell surface.
- The binding to an Fc fragment increases the half-life of muteins, which would give them an advantage with respect to small size drugs, since the doses and their frequency would be less.
- The binding to an Fc fragment of a human IgG1 that does not interacts with the Fc gamma receptors, except with neonatal Fc receptor, avoids the triggering of immune effector mechanisms on non-tumor cells of the host, reducing the potential for unexpected toxicities as compared with anti-receptor II antibodies which maintain their full ability to interact with Fc gamma receptors.

The present invention is further elaborated by the following examples and drawings. However, these examples should not be interpreted as limiting the scope of the invention.

BRIEF DESCRIPTION OF THE FIGURES

FIG. 6. G_M1 mutein inhibits the differentiation/conversion of naïve CD4+CD25−GITR− T cells into Foxp3+CD4+ regulatory T cells, which is induced by native TGFβ. The percentage of regulatory T cells recovered in the T cell cultures is reduced almost to zero when naïve T cells are incubated with 500 ng/ml of the mutein. This concentration is only 30 times higher than that of the recombinant human TGFβ1 used to primarily induce the conversion.

EXAMPLES

Example 1

Design of TGFβ Muteins

Figure 1:
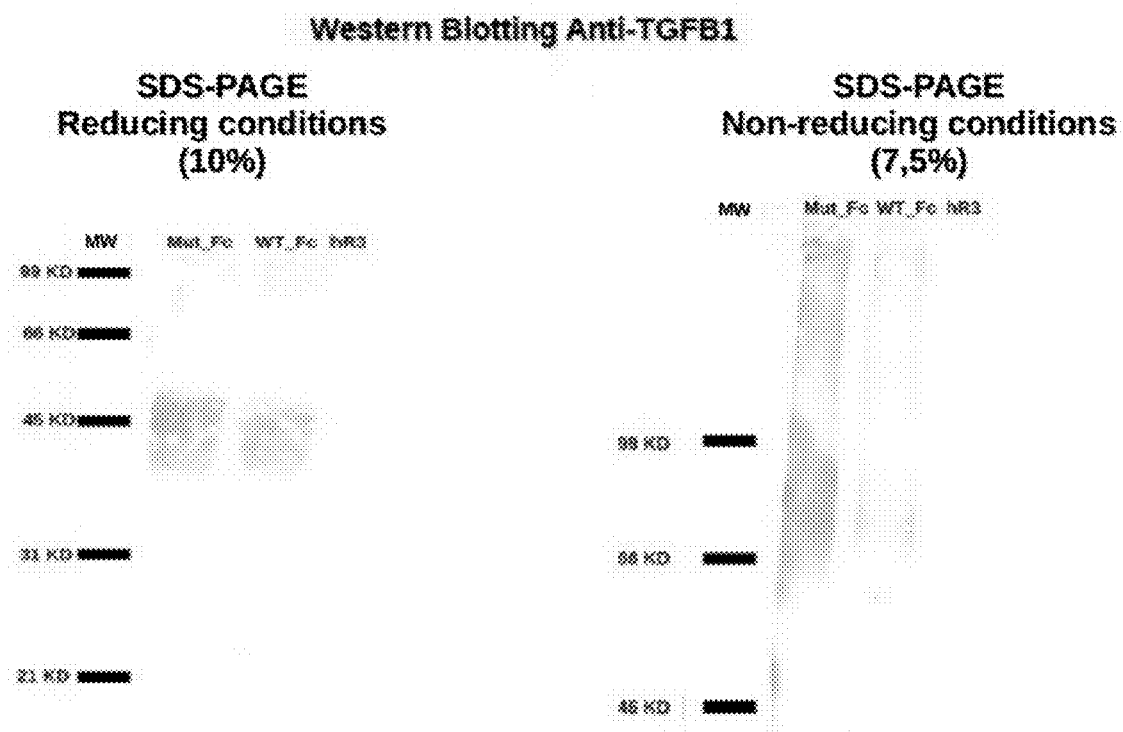
FIG. 1. Western blot analysis of the mutein G_M1 and TGFβ1. Wild type Fc-fusions proteins. The SDS-PAGE of these proteins was performed under non-reducing and reducing conditions, and the staining was made with an anti-human TGFβ1 antibody. First lane is loaded with a low molecular weight. protein standard, second lane is loaded with the mutein GM_1_Fc, third with TGFβ1 wild type Fc and the fourth with the irrelevant antibody hR3 was used.

The TGFβ mutants were designed computationally using bioinformatics techniques. As starting point the reported structures of the ternary complex of TGFβ1 and TGFβ3 with the TGFβ receptor were used. The energy of binding of the native isoforms and all possible mutated variants was determined using public bioinformatics programs. G_M1 mutein were expressed in the CHO-K1 cells using a genetic construct based in the lentiviral vector PLW that included the C-terminal hinge region and the domains Cγ2 and Cγ3 of a human IgG1 and a histidine tail. G_M1 was purified by affinity chromatography with protein A. It was obtained (FIG. 1) with high purity (>95%).

Example 2

Evaluation of the Binding of the Mutein G_M1 to TβRII by ELISA

Figure 2:
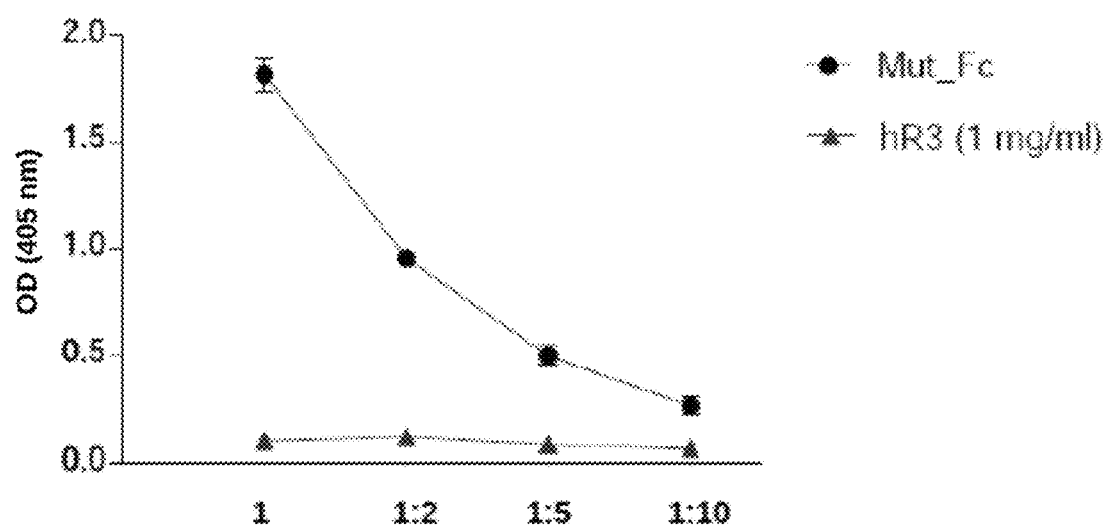
FIG. 2. ELISA assay to evaluate the TβRII receptor recognition by the G_M1_Fc mutein. As a negative control the irrelevant antibody hR3 was used. G_M1 mutein retains a binding capacity to TβRII receptor, which is similar to that of native TGFβ1.

An ELISA assay was performed coating with TβRII (1 ug/ml) and revealed with anti-human Fc antibody coupled to alkaline phosphatase. As a negative control irrelevant antibody hR3 was used. FIG. 2 shows that mutein G_M1 retains its binding capacity to TβRII receptor, which is similar to that of native TGFβ1.

Example 3

Mutein G_M1 have a Reduced Capacity to Signal through Receptor TβRI (ALK5), and Therefore to Mimic the Native TGFβ Biological Activity We compared the inhibition of IL2-dependent CTLL-2 cell line proliferation, induced by mutant or native TGFβ. 5000 CTLL-2 cells/wells were stimulated with rIL-2 (50U/ml) and cultured in the presence of the indicated concentrations of TGFβ1 wild type or mutein G_M1, for 48 h. Later alamar blue reagent was added to the culture and its reduction was measured at 540 and 630 nm.

Figure 3:
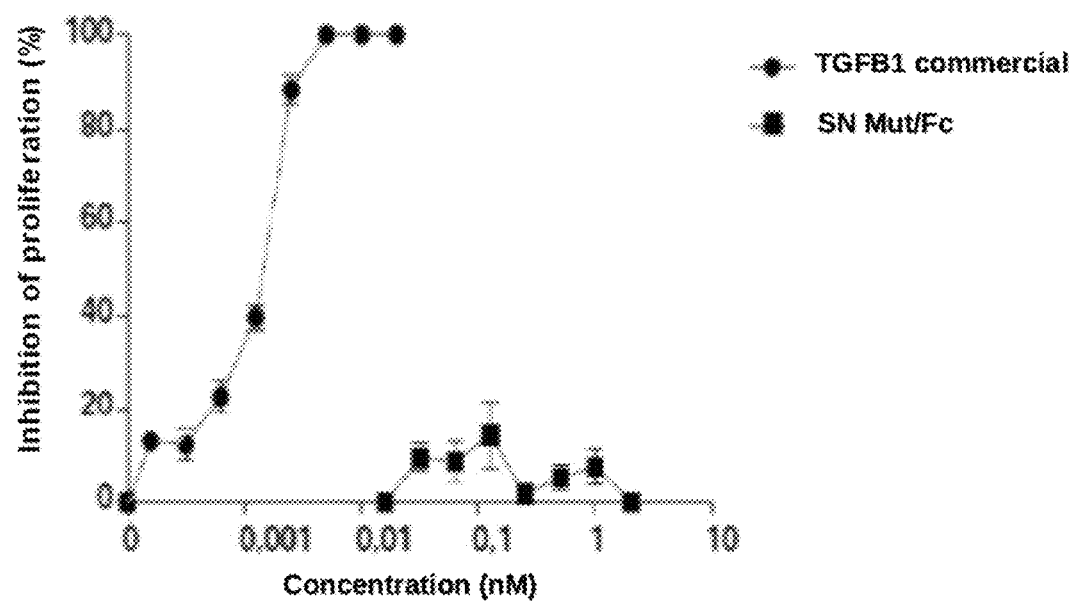
FIG. 3. Assay to evaluate the inhibition of IL2-dependent CTLL-2 cell line proliferation, induced by mutant or native TGFβ. It is shown that the ability of the mutein G_M1 to inhibit CTLL-2 cell line proliferation is much lower than that of human native TGFβ1. Data are expressed as the mean percentage of inhibition from three independent experiments.

G_M1 mutein was unable to inhibit proliferation of CTLL-2 line, at concentrations 200 times greater than those of commercial TGFβ1 used as positive control of the experiment (FIG. 3). It is shown that the ability of the mutein G_M1 to inhibit CTLL-2 cell line proliferation is much lower than that of commercial TGFβ1.

Example 4

Mutein G_M1 is Antagonist of TGFβ Signaling In Vitro

5000 CTLL-2 cells/wells were stimulated with rIL-2 (50U/ml) and cultured in the presence of 2 pM of TGFβ1 wild type and indicated concentrations of G_M1, or isotype control hR3 MAb; or anti-TGFβ1 antibody as a positive control. After 48 hour, alamar blue reagent was added to the culture and its reduction was measured at 540 and 630 nm.

Figure 4:
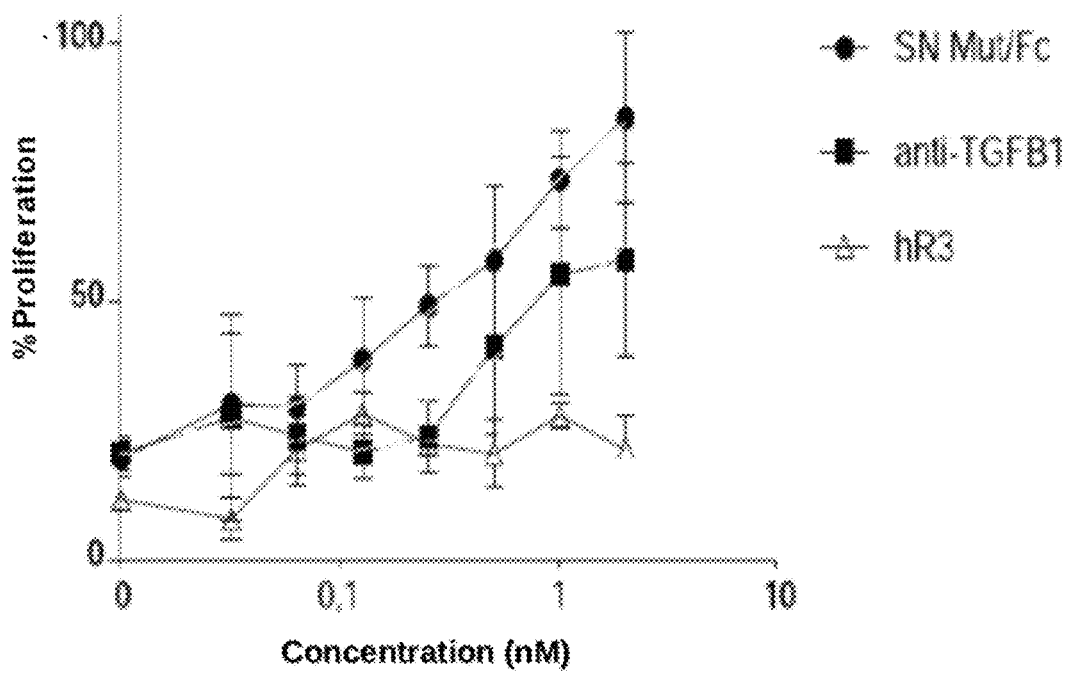
FIG. 4. Assay to evaluate the capacity of G_M1 mutein to neutralize the inhibition of IL2-dependent CTLL-2 cell line proliferation, caused by native TGF β1. The figure shows the mean percentage of cell proliferation scored in three independent experiments.

The G_M1 mutein, but not the isotype control MAb hR3, neutralizes the inhibition of IL2-dependent CTLL-2 cell line proliferation, caused by native TGFβ1 (FIG. 4). The neutralizing effect caused by the mutein is similar to that obtained with an anti-TGFβ1 antibody, which was used as positive control of the experiment.

Example 5

The Mutein G_M1 has Anti-Tumor Effect In Vitro

Figure 5:
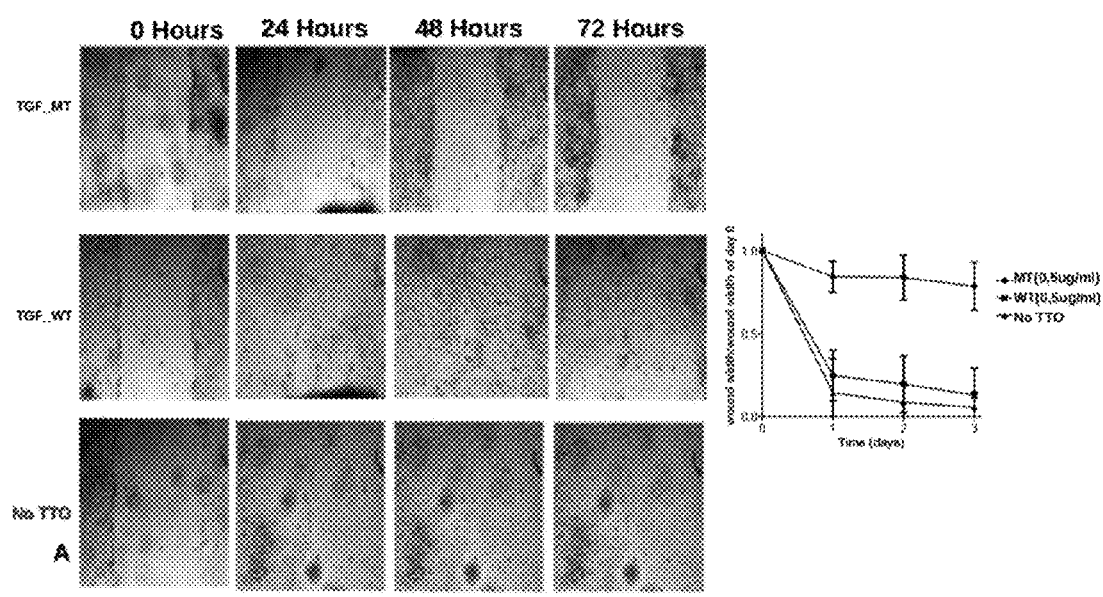
FIG. 5. G_M1 mutein inhibits in vitro the migration of murine 4T1 tumor cell line. Pictures of the wound closure were taken at various time intervals as is indicated in the Figure which shows that the rate of wound closure is significantly lower at each time point when the cells are treated with the mutein.

The ability of the mutein G_M1 to inhibit migration of murine tumor cell line 4T1 was evaluated in an in vitro wound healing assay (C C Liang et al, Nat Protoc. Two (2): 329-33, 2007). Confluent cells were wounded by scraping the cell monolayer with a sterile pipette tip. G_M1 mutein or TGFβ1 wild type (as negative control) was added to the well. FIG. 5 shows that the rate of wound closure is significantly lower ($p<0.05$ Kruskal-Wallis test with Dunn's post-test at each time point) when the cells are treated with the mutein.

Example 6

The Mutein G_M1 Inhibits the Differentiation of Naive CD4+ T Cells into Regulatory Foxp3+CD4+ T Cells Induced by Native TGF β1 and IL2

CD4+CD25−GITR− naive population from the spleen of 4 C57/BL6 mice was purified by cells sorting. $5\times10^4$ of these cells were stimulated with 3 μg/mL plate bound anti-CD3 and 3 μg/mL of soluble anti-CD28, in presence of 5 ng/ml IL-2 and 5 ng/ml of native human TGFβ1. In this culture condition the percentage of regulatory T cells recovered after 3 days was of 55.6%. The effect of the mutein in this culture was evaluated at concentrations of 250 and 500 ng/mL. The percentage of Foxp3+ regulatory T cells recovered, in the presence or absence of the mutein was measured. FIG. 6 shows how the percentage of regulatory T cells recovered in the T cell cultures is reduced almost to zero in the presence of G_M1 mutein.

The invention claimed is:

1. A mutant TGFβ1 or mutant TGFβ3 polypeptide that antagonizes the activity of TGFβ mediated by the ALK5 receptor, wherein, if said polypeptide is the mutant TGFβ1 polypeptide, it comprises an amino acid substitution in amino acid residues W30, L101 and I51 of mature TGFβ1; and wherein, if said polypeptide is the mutant TGBβ3 polypeptide, it comprises an amino acid substitution in amino acid residues W30, L101 and L51 of mature TGFβ3.

2. The polypeptide of claim 1 wherein the residues are substituted by amino acid residues selected from the group consisting of:
    for position 30: N,R,K,D,Q,L,S,P,V,I,G,C,T,A,E;
    for position 101: A, E; and
    for position 51: Q,W,Y,A.

3. The polypeptide according to claim 1 coupled to a fragment of human IgG1 comprising the mutations ala234 and ala235 in the Cγ2 domain.

4. A pharmaceutical composition comprising;
    at least one polypeptide of claim 1 in a range between

SEQUENCE LISTING

```
<160> NUMBER OF SEQ ID NOS: 73

<210> SEQ ID NO 1
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 1

Ala Leu Asp Thr Asp Ala Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Tyr Trp Ser Leu Asp Thr Gln Thr Ser Lys Val Leu Ala Leu
    50                  55                  60

Tyr Asn Gln His Asn Pro Gly Ala Ser Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 2
<211> LENGTH: 112
<212> TYPE: PRT
<213> ORGANISM: Artificial Sequence
<220> FEATURE:
<223> OTHER INFORMATION: by DNA recombinant technology
```

<400> SEQUENCE: 2

Ala Leu Asp Ala Ala Ala Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
        50                  55                  60

Tyr Asn Thr Ile Asn Pro Glu Ala Ser Ala Ser Pro Cys Cys Val Ser
65              70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 3
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 3

Ala Leu Asp Thr Asn Ala Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
        50                  55                  60

Tyr Asn Thr Leu Asn Pro Glu Ala Ser Ala Ser Pro Cys Cys Val Pro
65              70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 4
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 4

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Asn Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65              70                  75                  80

```
Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 5
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 5

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Arg Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 6
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 6

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Lys Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 7
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 7

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Asp Lys Trp
            20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 8

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Gln Lys Trp
            20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 9
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 9

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Leu Lys Trp
            20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

```
Lys Val Glu Gln Leu Ser Asn Met Ile Val Arg Ser Cys Lys Cys Ser
            100                 105                 110
```

```
<210> SEQ ID NO 10
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 10

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Ser Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

```
<210> SEQ ID NO 11
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 11

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Pro Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

```
<210> SEQ ID NO 12
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 12

Ala Leu Asp Thr Asn Tyr Cys Phe Ser Ser Thr Glu Lys Asn Cys Cys
1               5                   10                  15
```

Val Arg Gln Leu Tyr Ile Asp Phe Arg Lys Asp Leu Gly Val Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 13

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Ile Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 14

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Gly Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 15

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Cys Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 16

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Thr Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 17
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 17

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Ala Lys Trp
            20                  25                  30
```

```
Ile His Glu Pro Lys Gly Tyr His Ala Asn Phe Cys Leu Gly Pro Cys
         35                  40                  45

Pro Tyr Ile Trp Ser Leu Asp Thr Gln Tyr Ser Lys Val Leu Ala Leu
 50                  55                  60

Tyr Asn Gln His Asn Pro Gly Ala Ser Ala Ala Pro Cys Cys Val Pro
 65                  70                  75                  80

Gln Ala Leu Glu Pro Leu Pro Ile Val Tyr Tyr Val Gly Arg Lys Pro
                 85                  90                  95

Lys Val Glu Gln Leu Ser Asn Met Ile Val Arg Ser Cys Lys Cys Ser
                100                 105                 110

<210> SEQ ID NO 18
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 18

Ala Leu Asp Thr Asn Tyr Cys Phe Ser Ser Thr Glu Lys Asn Cys Cys
 1                   5                  10                  15

Val Arg Gln Leu Tyr Ile Asp Phe Arg Lys Asp Leu Gly Glu Lys Trp
                 20                  25                  30

Ile His Glu Pro Lys Gly Tyr His Ala Asn Phe Cys Leu Gly Pro Cys
             35                  40                  45

Pro Tyr Ile Trp Ser Leu Asp Thr Gln Tyr Ser Lys Val Leu Ala Leu
 50                  55                  60

Tyr Asn Gln His Asn Pro Gly Ala Ser Ala Ala Pro Cys Cys Val Pro
 65                  70                  75                  80

Gln Ala Leu Glu Pro Leu Pro Ile Val Tyr Tyr Val Gly Arg Lys Pro
                 85                  90                  95

Lys Val Glu Gln Leu Ser Asn Met Ile Val Arg Ser Cys Lys Cys Ser
                100                 105                 110

<210> SEQ ID NO 19
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 19

Ala Leu Asp Ala Ala Tyr Cys Phe Arg Asn Val Gln Asp Asn Cys Cys
 1                   5                  10                  15

Leu Arg Pro Leu Tyr Ile Asp Phe Lys Arg Asp Leu Gly Asn Lys Trp
                 20                  25                  30

Ile His Glu Pro Lys Gly Tyr Asn Ala Asn Phe Cys Ala Gly Ala Cys
             35                  40                  45

Pro Tyr Leu Trp Ser Ser Asp Thr Gln His Ser Arg Val Leu Ser Leu
 50                  55                  60

Tyr Asn Thr Ile Asn Pro Glu Ala Ser Ala Ser Pro Cys Cys Val Ser
 65                  70                  75                  80

Gln Asp Leu Glu Pro Leu Thr Ile Leu Tyr Tyr Ile Gly Lys Thr Pro
                 85                  90                  95

Lys Ile Glu Gln Leu Ser Asn Met Ile Val Lys Ser Cys Lys Cys Ser
                100                 105                 110

<210> SEQ ID NO 20
```

<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 20

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Arg Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 21

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Lys Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 22

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Asp Lys Trp
            20                  25                  30

Ile His Glu Pro Lys Gly Tyr Asn Ala Asn Phe Cys Ala Gly Ala Cys
        35                  40                  45

```
Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 23

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Gln Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 24

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Leu Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 25
<211> LENGTH: 112
<212> TYPE: PRT
<213> ORGANISM: Artificial Sequence
```

```
<220> FEATURE:
<223> OTHER INFORMATION: by DNA recombinant technology

<400> SEQUENCE: 25

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Ser Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65              70                  75                  80

Gln Asp Leu Glu Pro Leu Thr Ile Leu Tyr Tyr Ile Gly Lys Thr Pro
            85                  90                  95

Lys Ile Glu Gln Leu Ser Asn Met Ile Val Lys Ser Cys Lys Cys Ser
            100                 105                 110

<210> SEQ ID NO 26
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 26

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Pro Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65              70                  75                  80

Gln Asp Leu Glu Pro Leu Thr Ile Leu Tyr Tyr Ile Gly Lys Thr Pro
            85                  90                  95

Lys Ile Glu Gln Leu Ser Asn Met Ile Val Lys Ser Cys Lys Cys Ser
            100                 105                 110

<210> SEQ ID NO 27
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 27

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Val Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60
```

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 28

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Ile Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
        50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 29

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Gly Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
        50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 30

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Cys Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65              70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 31
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 31

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Thr Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65              70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 32
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 32

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Ala Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65              70                  75                  80
```

```
Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 33
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 33

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Glu Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 34
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 34

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Asn Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 35
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 35

```
Ala Leu Asp Thr Asn Tyr Cys Phe Arg Asn Leu Glu Glu Asn Cys Cys
```

```
1               5                   10                  15
Val Arg Pro Leu Tyr Ile Asp Phe Arg Gln Asp Leu Gly Arg Lys Trp
            20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
            50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
                100                 105                 110
```

<210> SEQ ID NO 36
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 36

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Lys Lys Trp
            20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
            50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
                100                 105                 110
```

<210> SEQ ID NO 37
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 37

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Asp Lys Trp
            20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
            50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95
```

```
Lys Val Glu Gln Leu Ser Asn Met Val Val Lys Ser Cys Lys Cys Ser
            100                 105                 110
```

<210> SEQ ID NO 38
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 38

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Gln Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 39
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 39

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Leu Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 40
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 40

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Ser Lys Trp
```

```
                20                  25                  30
Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
        50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 41
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 41

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Pro Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 42

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Val Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

```
<210> SEQ ID NO 43
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 43
```

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Ile Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

```
<210> SEQ ID NO 44
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 44
```

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Gly Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

```
<210> SEQ ID NO 45
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 45
```

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Cys Lys Trp
            20                  25                  30

Val His Glu Pro Lys Gly Tyr Tyr Ala Asn Phe Cys Ser Gly Pro Cys

```
                35                  40                  45
Pro Tyr Leu Arg Ser Ala Asp Thr Thr His Ser Thr Val Leu Gly Leu
 50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
                100                 105                 110

<210> SEQ ID NO 46
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 46

Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Thr Lys Trp
                 20                  25                  30

Val His Glu Pro Lys Gly Tyr Tyr Ala Asn Phe Cys Ser Gly Pro Cys
                 35                  40                  45

Pro Tyr Leu Arg Ser Ala Asp Thr Thr His Ser Thr Val Leu Gly Leu
 50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
                100                 105                 110

<210> SEQ ID NO 47
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 47

Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Ala Lys Trp
                 20                  25                  30

Val His Glu Pro Lys Gly Tyr Tyr Ala Asn Phe Cys Ser Gly Pro Cys
                 35                  40                  45

Pro Tyr Leu Arg Ser Ala Asp Thr Thr His Ser Thr Val Leu Gly Leu
 50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
                100                 105                 110

<210> SEQ ID NO 48
<211> LENGTH: 112
```

<212> TYPE: PRT
<213> ORGANISM: Artificial Sequence
<220> FEATURE:
<223> OTHER INFORMATION: by DNA recombinant technology

<400> SEQUENCE: 48

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Glu Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 49
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 49

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Ala
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 50
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 50

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Ala
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
```

```
                 50                  55                  60

Tyr Asn Thr Ile Asn Pro Glu Ala Ser Ala Ser Pro Cys Cys Val Ser
 65                  70                  75                  80

Gln Asp Leu Glu Pro Leu Thr Ile Leu Tyr Tyr Ile Gly Lys Thr Pro
                     85                  90                  95

Lys Ile Glu Gln Leu Ser Asn Met Ile Val Lys Ser Cys Lys Cys Ser
                    100                 105                 110

<210> SEQ ID NO 51
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 51

Ala Leu Asp Thr Asn Tyr Cys Phe Arg Asn Leu Glu Glu Asn Cys Cys
  1               5                  10                  15

Val Arg Pro Leu Tyr Ile Asp Phe Arg Gln Asp Leu Gly Trp Lys Ala
                 20                  25                  30

Val His Glu Pro Lys Gly Tyr Tyr Ala Asn Phe Cys Ser Gly Pro Cys
                 35                  40                  45

Pro Tyr Leu Arg Ser Ala Asp Thr Thr His Ser Thr Val Leu Gly Leu
 50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                     85                  90                  95

Lys Val Glu Gln Leu Ser Asn Met Val Val Lys Ser Cys Lys Cys Ser
                    100                 105                 110

<210> SEQ ID NO 52
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 52

Ala Leu Asp Thr Asn Tyr Cys Phe Ser Ser Thr Glu Lys Asn Cys Cys
  1               5                  10                  15

Val Arg Gln Leu Tyr Ile Asp Phe Arg Lys Asp Leu Gly Trp Lys Trp
                 20                  25                  30

Ile His Glu Pro Lys Gly Tyr His Ala Asn Phe Cys Leu Gly Pro Cys
                 35                  40                  45

Pro Tyr Gln Trp Ser Leu Asp Thr Gln Tyr Ser Lys Val Leu Ala Leu
 50                  55                  60

Tyr Asn Gln His Asn Pro Gly Ala Ser Ala Ala Pro Cys Cys Val Pro
 65                  70                  75                  80

Gln Ala Leu Glu Pro Leu Pro Ile Val Tyr Tyr Val Gly Arg Lys Pro
                     85                  90                  95

Lys Val Glu Gln Leu Ser Asn Met Ile Val Arg Ser Cys Lys Cys Ser
                    100                 105                 110

<210> SEQ ID NO 53
<211> LENGTH: 112
<212> TYPE: PRT
<213> ORGANISM: Artificial Sequence
<220> FEATURE:
```

<223> OTHER INFORMATION: by DNA recombinant technology

<400> SEQUENCE: 53

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Trp Trp Ser Leu Asp Thr Gln Tyr Ser Lys Val Leu Ala Leu
50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 54
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 54

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Tyr Trp Ser Leu Asp Thr Gln Tyr Ser Lys Val Leu Ala Leu
50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 55
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 55

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ala Trp Ser Leu Asp Thr Gln Tyr Ser Lys Val Leu Ala Leu
50                  55                  60

Tyr Asn Gln His Asn Pro Gly Ala Ser Ala Ala Pro Cys Cys Val Pro
```

```
                 65                  70                  75                  80

Gln Ala Leu Glu Pro Leu Pro Ile Val Tyr Tyr Val Gly Arg Lys Pro
                 85                  90                  95

Lys Val Glu Gln Leu Ser Asn Met Ile Val Arg Ser Cys Lys Cys Ser
                100                 105                 110

<210> SEQ ID NO 56
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 56

Ala Leu Asp Ala Ala Tyr Cys Phe Arg Asn Val Gln Asp Asn Cys Cys
1               5                  10                  15

Leu Arg Pro Leu Tyr Ile Asp Phe Lys Arg Asp Leu Gly Trp Lys Trp
                20                  25                  30

Ile His Glu Pro Lys Gly Tyr Asn Ala Asn Phe Cys Ala Gly Ala Cys
            35                  40                  45

Pro Tyr Gln Trp Ser Ser Asp Thr Gln His Ser Arg Val Leu Ser Leu
        50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
                100                 105                 110

<210> SEQ ID NO 57
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 57

Ala Leu Asp Ala Ala Tyr Cys Phe Arg Asn Val Gln Asp Asn Cys Cys
1               5                  10                  15

Leu Arg Pro Leu Tyr Ile Asp Phe Lys Arg Asp Leu Gly Trp Lys Trp
                20                  25                  30

Ile His Glu Pro Lys Gly Tyr Asn Ala Asn Phe Cys Ala Gly Ala Cys
            35                  40                  45

Pro Tyr Trp Trp Ser Ser Asp Thr Gln His Ser Arg Val Leu Ser Leu
        50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
                100                 105                 110

<210> SEQ ID NO 58
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 58
```

-continued

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Tyr Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65              70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 59

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Ala Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65              70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 60

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Gln Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65              70                  75                  80

Gln Asp Leu Glu Pro Leu Thr Ile Leu Tyr Tyr Val Gly Arg Thr Pro

```
                    85                  90                  95

Lys Val Glu Gln Leu Ser Asn Met Val Val Lys Ser Cys Lys Cys Ser
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 61

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Trp Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 62

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Tyr Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 63

Ala Leu Asp Thr Asn Tyr Cys Phe Arg Asn Leu Glu Glu Asn Cys Cys
1               5                   10                  15
```

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
            35                  40                  45

Pro Tyr Ala Arg Ser Ala Asp Thr Thr His Ser Thr Val Leu Gly Leu
 50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 64
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 64

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
 50                  55                  60

Tyr Asn His His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 65
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 65

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
 50                  55                  60

Tyr Asn Phe His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser

<210> SEQ ID NO 66
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 66

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Tyr His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 67
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 67

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Trp His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 68
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 68

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
 50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Ala Ser Asn Met Ile Val Arg Ser Cys Lys Cys Ser
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 69

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
 50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Glu Ser Asn Met Ile Val Arg Ser Cys Lys Cys Ser
            100                 105                 110

<210> SEQ ID NO 70
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 70

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
 50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Ala Ser Asn Met Ile Val Lys Ser Cys Lys Cys Ser
            100                 105                 110

-continued

```
<210> SEQ ID NO 71
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 71

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Glu Ser Asn Met Ile Val Lys Ser Cys Lys Cys Ser
            100                 105                 110

<210> SEQ ID NO 72
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 72

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Ala Ser Asn Met Val Val Lys Ser Cys Lys Cys Ser
            100                 105                 110

<210> SEQ ID NO 73
<211> LENGTH: 112
<212> TYPE: PRT
<213> ORGANISM: Artificial Sequence
<220> FEATURE:
<223> OTHER INFORMATION: by DNA recombinant technology

<400> SEQUENCE: 73

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45
```

```
Pro Tyr Leu Arg Ser Ala Asp Thr Thr His Ser Thr Val Leu Gly Leu
    50              55                  60

Tyr Asn Thr Leu Asn Pro Glu Ala Ser Ala Ser Pro Cys Cys Val Pro
65              70                  75                      80

Gln Asp Leu Glu Pro Leu Thr Ile Leu Tyr Tyr Val Gly Arg Thr Pro
                85                  90                  95

Lys Val Glu Gln Glu Ser Asn Met Val Val Lys Ser Cys Lys Cys Ser
            100             105             110
```